(12) United States Patent
Ishida et al.

(10) Patent No.: US 9,855,345 B2
(45) Date of Patent: Jan. 2, 2018

(54) METHOD FOR PRODUCING LIPOPLEX FOR TOPICAL ADMINISTRATION AND ANTITUMOR AGENT USING SUCH LIPOPLEX

(71) Applicant: DELTA-FLY PHARMA, INC., Tokushima-shi, Tokushima (JP)

(72) Inventors: Tatsuhiro Ishida, Tokushima (JP); Kiyoshi Eshima, Tokushima (JP); Masakazu Fukushima, Otsu (JP)

(73) Assignee: DELTA-FLY PHARMA, INC., Tokushima-Shi (JP)

( * ) Notice: Subject to any disclaimer, the term of this patent is extended or adjusted under 35 U.S.C. 154(b) by 0 days.

(21) Appl. No.: 15/523,222

(22) PCT Filed: Oct. 28, 2015

(86) PCT No.: PCT/JP2015/080316
§ 371 (c)(1),
(2) Date: Apr. 28, 2017

(87) PCT Pub. No.: WO2016/068160
PCT Pub. Date: May 6, 2016

(65) Prior Publication Data
US 2017/0319713 A1 Nov. 9, 2017

(30) Foreign Application Priority Data
Oct. 30, 2014 (JP) .................. 2014-221062

(51) Int. Cl.
*A61K 48/00* (2006.01)
*A61K 9/127* (2006.01)
*A61K 31/7105* (2006.01)
*A61K 31/513* (2006.01)

(52) U.S. Cl.
CPC ............ *A61K 48/005* (2013.01); *A61K 9/127* (2013.01); *A61K 31/513* (2013.01); *A61K 31/7105* (2013.01); *A61K 48/0075* (2013.01); *C12N 2310/14* (2013.01); *C12N 2320/30* (2013.01)

(58) Field of Classification Search
CPC ... A61K 47/6911; A61K 9/127; A61K 31/713
See application file for complete search history.

(56) References Cited

U.S. PATENT DOCUMENTS

| | | | |
|---|---|---|---|
| 5,744,159 | A | 4/1998 | Yagi et al. |
| 9,745,583 | B2 * | 8/2017 | Ishida ............... A61K 47/6911 |
| 2002/0111326 | A1 | 8/2002 | Tanaka et al. |
| 2008/0306153 | A1 | 12/2008 | Panzner et al. |
| 2010/0112042 | A1 | 5/2010 | Polisky et al. |
| 2011/0229581 | A1 | 9/2011 | Zhao et al. |
| 2012/0016012 | A1 | 1/2012 | Wada et al. |
| 2012/0301537 | A1 | 11/2012 | Ishida et al. |
| 2016/0208263 | A1 | 7/2016 | Ishida |

FOREIGN PATENT DOCUMENTS

| | | |
|---|---|---|
| CN | 103561775 A | 2/2014 |
| EP | 2 716 304 A1 | 4/2014 |
| JP | 9-248182 A | 9/1997 |
| JP | 2007-524667 A | 8/2007 |
| JP | 2010-513354 A | 4/2010 |
| JP | 2012-505913 A | 3/2012 |
| TW | 201021853 A1 | 6/2010 |
| TW | 201300113 A | 1/2013 |
| WO | WO 98/45463 A1 | 10/1998 |
| WO | WO 2005/067632 A2 | 7/2005 |
| WO | WO 2006/048329 A1 | 5/2006 |
| WO | WO 2008/074487 A2 | 6/2008 |
| WO | WO 2010/113844 A1 | 10/2010 |
| WO | WO 2012/161196 A1 | 11/2012 |
| WO | WO 2013/149140 A1 | 10/2013 |
| WO | WO 2013/177419 A2 | 11/2013 |
| WO | WO 2014/178152 A1 | 11/2014 |

OTHER PUBLICATIONS

Candiani et al., "Bioreducible Liposomes for Gene Delivery: From the Formulation to the Mechanism of Action," PLoS ONE (Oct. 2010), vol. 5, No. 10, e 13430, pp. 1-8.
Chinese Office Action issued in Patent Application No. 201380075820.0 dated Jan. 24, 2017.
European Journal of Cancer, 24th EORTC-NCI-AACR Symposium on Molecular Targets and Cancer Therapeutics, vol. 48, Supplement 6, Nov. 2012, pp. 69-70.
International Search Report issued in PCT/JP2013/080367, dated Jan. 7, 2014.
International Search Report issued in PCT/JP2015/080316 dated Jan. 26, 2016.
Ishida et al., "An entirely novel nanoparticle carrying a bioactive shRNA molecule (DFP-10825) could be clinically effective against the high risk patients with mesothelioma relapsed or refractory after treatment with pemetrexed based chemotherapy" 24th EORTC-NCI-AACR Symposium on Molecular Targets and Cancer Therapeutics, Nov. 7, 2012, 1 page.
Kikuchi, A., et al., "Development of Novel Cationic Liposomes for Efficient Gene Transfer into Peritoneal Disseminated Tumor," Human Gene Therapy, Apr. 10, 1999, vol. 10, pp. 947-955.
Leng et al., "Advances in Systemic siRNA Delivery", Drugs Future., vol. 34, No. 9, Sep. 2009, pp. 1-30.
Ma et al., "Paclitaxel Nano-Delivery Systems: A Comprehensive Review", Nanomedicine & Nanotechnology, vol. 4, Issue 2, 2013, 16 pages (with English-language Translation).

(Continued)

*Primary Examiner* — J. E. Angell
(74) *Attorney, Agent, or Firm* — Birch, Stewart, Kolasch & Birch, LLP

(57) ABSTRACT

An object of this invention is to provide a novel delivery means that enables efficient delivery of an active ingredient to a target cell. Such objective is attained by a lipoplex comprising dioleylphosphatidylethanolamine (DOPE), phosphatidylcholine, a cationic lipid, and an RNAi molecule and an industrial method for producing the same.

4 Claims, 12 Drawing Sheets

(56) References Cited

OTHER PUBLICATIONS

Nicol et al., "Effect of Phospholipid Composition on an Amphipathic Peptide-Mediated Pore Formation in Bilayer Vesicles," Biophysical Journal (Feb. 2000), vol. 78, pp. 818-829.
Office Action issued in Chinese Patent Application No. 201580001313.1 dated Feb. 17, 2017 (with English-language Translation).
Office Action issued in Taiwanese Patent Application No. 102140217 dated Oct. 27, 2014.
Office Action issued in Taiwanese Patent Application No. 104135644 dated Oct. 24, 2016.
Office Action dated Oct. 18, 2016, in Japanese Patent Application No. 2015-514740.
Ozpolat et al., "Nanomedicine based approaches for the delivery of siRNA in cancer", Journal of Internal Medicine, vol. 267, 2009, pp. 44-53.
Written Opinion issued in PCT/JP2013/080367, dated Jan. 7, 2014.
Wu et al., "Lipidic Systems for In Vivo siRNA Delivery", The AAPS Journal, vol. 11, No. 4, Dec. 2009, pp. 639-652.
International Search Report for PCT/JP2015/080316 (PCT/ISA/210) dated Jan. 26, 2016.
Written Opinion of the International Searching Authority for PCT/JP2015/080316 (PCT/ISA/237) dated Jan. 26, 2016.

\* cited by examiner

Fig. 1

| Sample | Particle diameter (nm) | Polydispersity index | Zeta potential (mV) |
|---|---|---|---|
| Conventional preparation | 488.9 ± 73.7 | 0.484 ± 0.100 | 33.3 ± 2.2 |
| Novel preparation (1) | 623.4 ± 55.9 | 0.548 ± 0.034 | 36.2 ± 2.5 |
| Novel preparation (2) | 651.5 ± 66.5 | 0.529 ± 0.014 | 34.7 ± 1.2 |

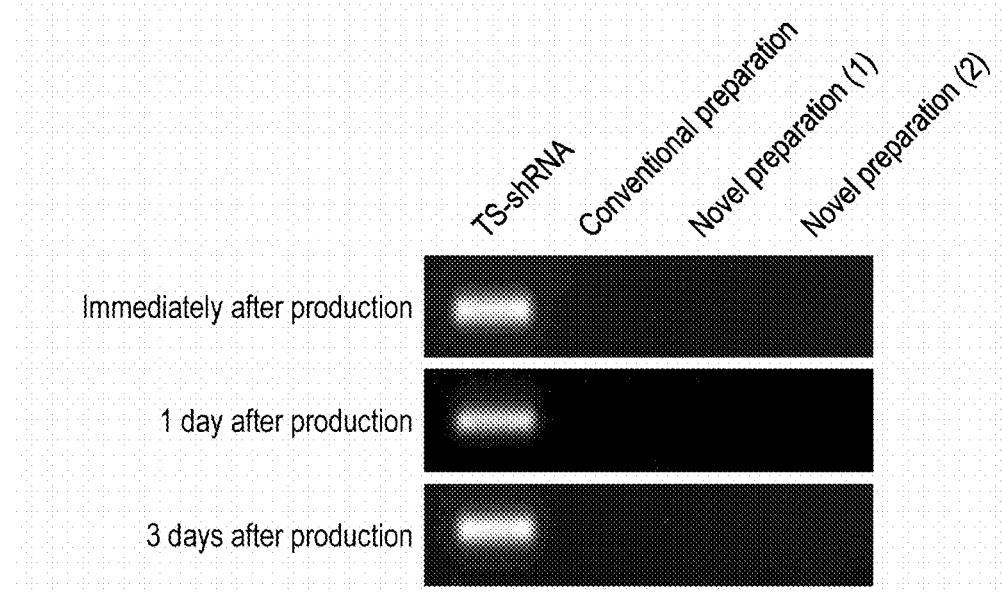

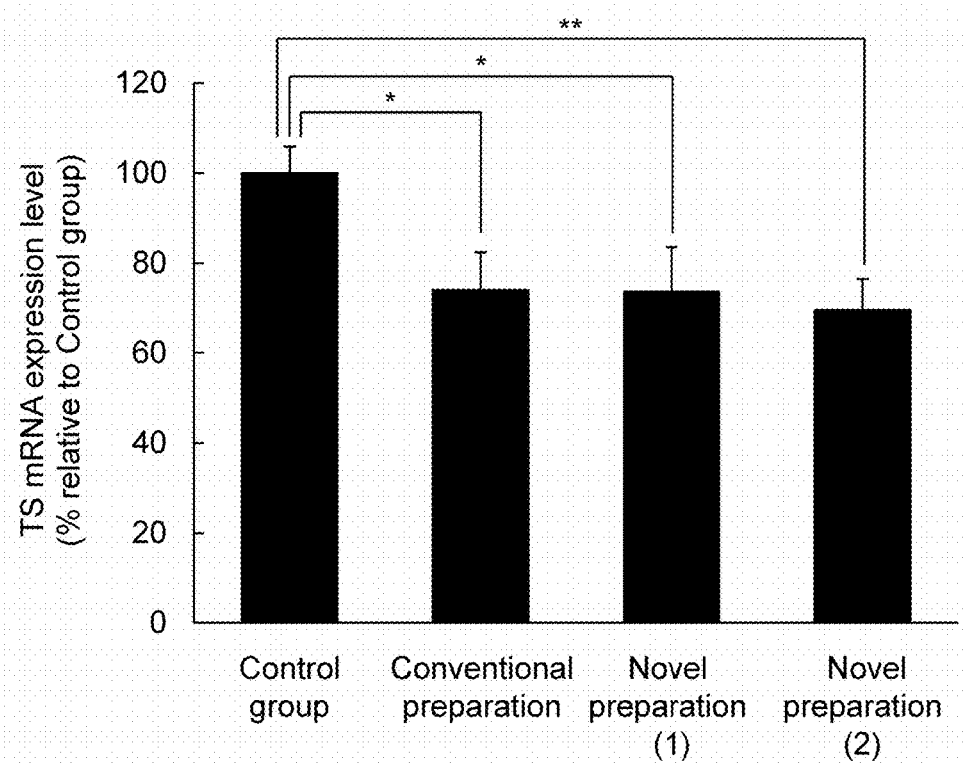

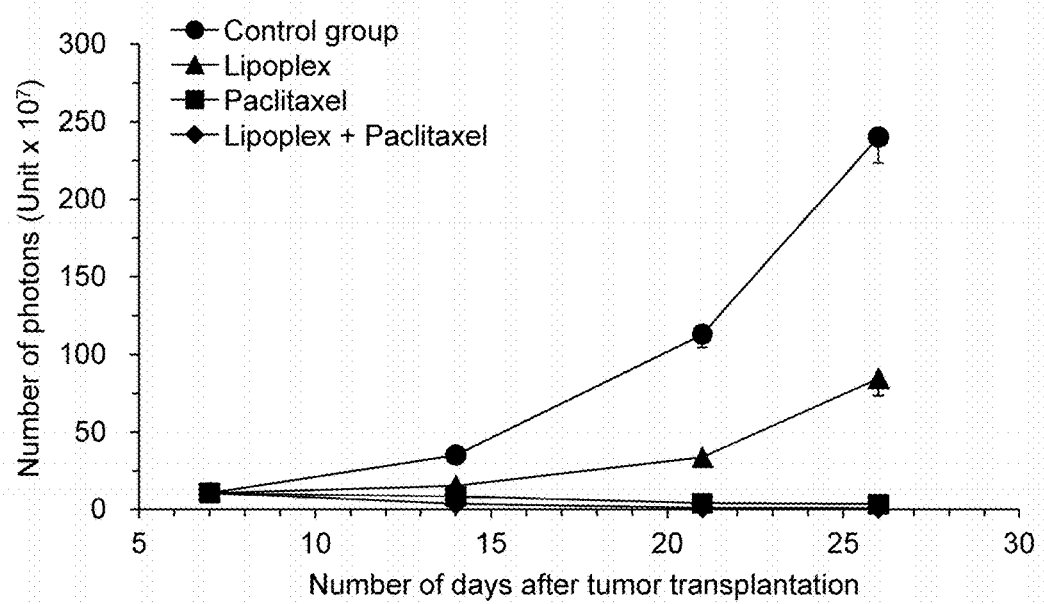

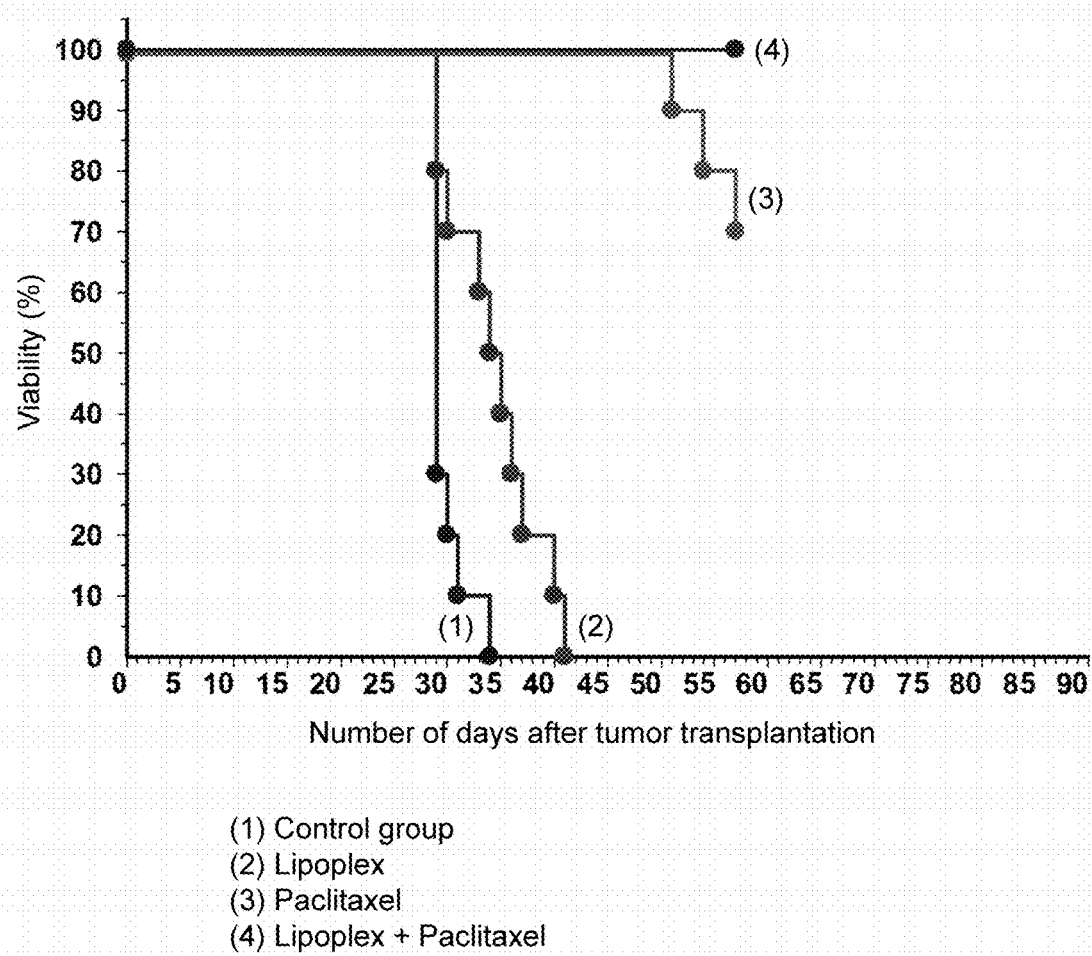

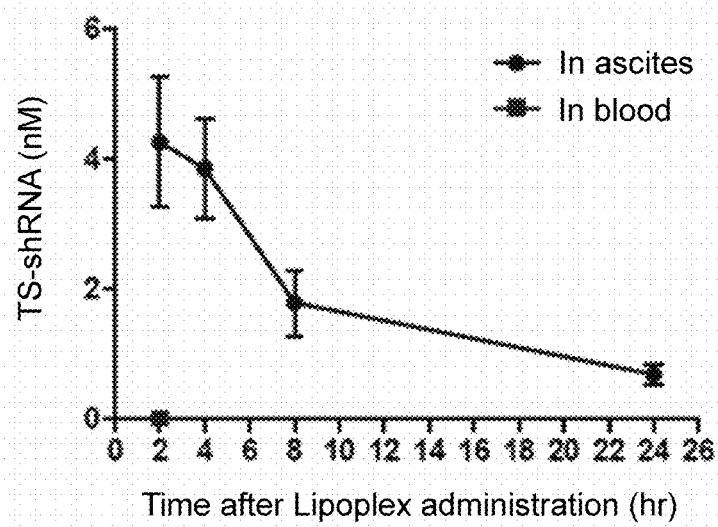

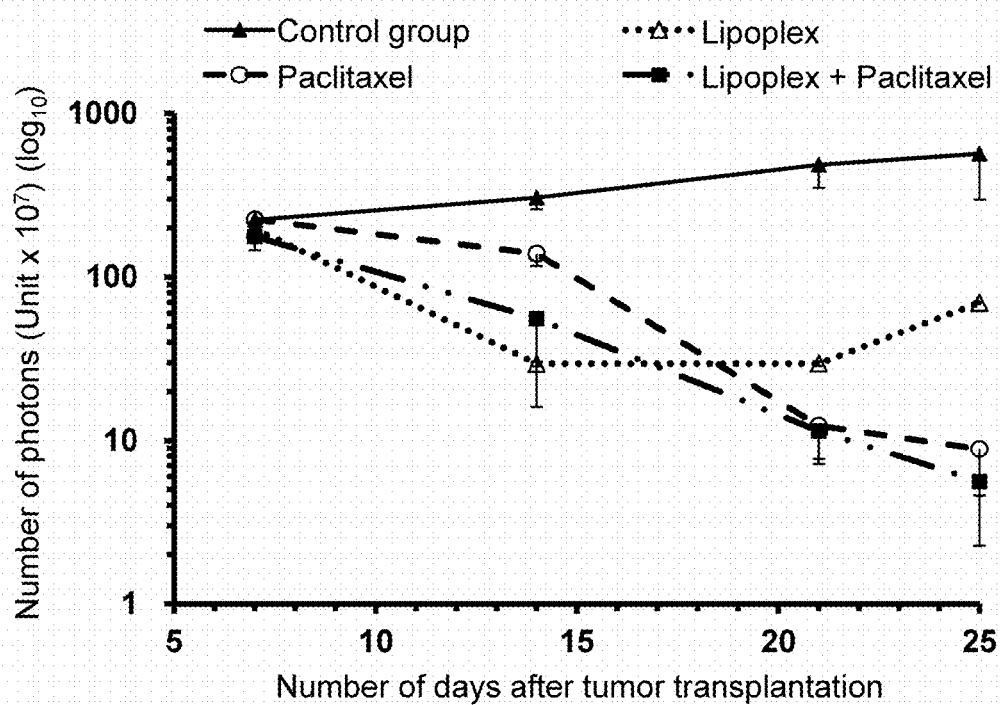

(1) Control group
(2) Lipoplex
(3) Paclitaxel
(4) Lipoplex + Paclitaxel

METHOD FOR PRODUCING LIPOPLEX FOR TOPICAL ADMINISTRATION AND ANTITUMOR AGENT USING SUCH LIPOPLEX

TECHNICAL FIELD

The present invention relates to a novel method for producing a lipoplex used for topical administration and an antitumor agent using such lipoplex.

BACKGROUND ART

Liposomes are composed of phospholipids that constitute the cell membranes of organisms, they have high biocompatibility, and they can deliver drugs and active ingredients while protecting them from degrading enzymes in vivo. Accordingly, liposomes have gained attention as useful tools for drug delivery systems.

Meanwhile, RNAi molecules that induce RNA interference (hereafter referred to as "RNAi") have gained attention as useful tools for tumor treatment and other purposes, and a wide variety of RNAi molecules that are capable of tumor growth inhibition have been developed. In addition, a method of using complexes composed of RNAi molecules and lipid mixtures (i.e., lipoplexes) to deliver RNAi molecules as active ingredients to tumor cells have been developed (Qixin Leng et al., Drug Future, September 2009; 34 (9): 721; Sherry Y., Wu et al., The AAPS Journal, Vol. 11, No. 4, December 2009; and B. Ozpolat et al., Journal of Internal Medicine 267; 44-53, 2009).

In the past, the present inventors developed RNAi molecules targeting thymidylate synthases (hereafter referred to as "TS"), which are involved with tumor growth (WO 2010/113844). They reported that delivery of such RNAi molecules to the tumors via, for example, intravenous administration with the use of complexes (lipoplexes) included in a cationic lipid mixture of a given formulation would make it possible to inhibit the growth of tumors showing TS expression. They also reported that the use of such lipoplexes in combination with chemotherapeutic agents would result in the improvement of tumor-targeting efficiency as well as the improvement of antitumor effects of RNAi molecules to a significant extent (WO 2012/161196).

SUMMARY OF THE INVENTION

Objects to be Attained by the Invention

According to a conventional technique of lipoplex production, a method for preparing a lipid mixture has comprised a step of dissolving a constituent, such as a phospholipid, in an organic solvent, such as chloroform or cyclohexane, in advance. In an industrial production method involving the use of an organic solvent, such as chloroform or cyclohexane, however, it has been necessary to provide large-scale facilities, such as facilities for hazardous material handling or explosion-proof apparatuses. In the past, also, lipoplex production had required a complicated process comprising preparing an aqueous solution of RNAi molecules, separately preparing a lipid mixture, and then mixing the aqueous solution with the lipid mixture prior to administration to a cancer patient at a prescription department of a hospital, with such process requiring extensive labor.

Given the above circumstances, it is an object of the present invention to provide an industrial method for lipoplex production that enables easy, simultaneous production of lipoplex-generating powders which produce lipoplex by merely suspending it in a solvent such as water. This would obviate the need for a complicated process of lipoplex production in which a lipid mixture would be generated by using a large quantity of an organic solvent, such as chloroform or cyclohexane, and being subjected to lyophilization, and the resulting lipid mixture would be dispersed in a solvent, such as water, following which the resulting dispersion would then be mixed with an aqueous solution of RNAi molecules.

It is another object of the present invention to eliminate the need for a complicated process of lipoplex preparation that requires extensive labor at a prescription department of a hospital.

Means for Attaining the Objects

The present inventors have conducted concentrated studies in order to attain the above objects. As a result, they have succeeded in producing a lyophilized lipoplex product by dissolving dioleylphosphatidylethanolamine (DOPE), phosphatidylcholine, and a cationic lipid in highly biotolerant and non-explosive alcohol, adding the alcohol solution dropwise to a solution of RNAi molecules with agitation and, lyophilizing the solution and removing a solvent such as alcohol therefrom. Thus, they discovered that a cancer patient could be effectively treated by mixing the resulting lyophilized product of the lipoplex obtained in an adequate buffer and topically administering the same to a target organ afflicted with cancer. The present invention is based on such findings.

The present invention is as described below.

[1] A method for producing a lipoplex comprising dioleylphosphatidylethanolamine (DOPE), phosphatidylcholine, a cationic lipid, and RNAi molecules, comprising steps of:

(a) dissolving dioleylphosphatidylethanolamine (DOPE), phosphatidylcholine, and a cationic lipid in alcohol;

(b) adding the alcohol solution obtained in (a) dropwise to a solution of RNAi molecules with agitation; and (c) lyophilizing the solution obtained in (b), wherein the phosphatidylcholine has one or more features selected from (i) to (iii) below:

(i) the phosphatidylcholine comprises at least one unsaturated fatty acid chain containing a carbon-to-carbon double bond;

(ii) the phosphatidylcholine comprises at least one unsaturated fatty acid chain containing a cis-form carbon-to-carbon double bond; and (iii) the phosphatidylcholine has a phase transition temperature below 0° C.

[2] The method according to [1], wherein the cationic lipid is O,O'-ditetradecanoyl-N-(α-trimethylammonioacetyl)diethanolamine chloride (DC-6-14).

[3] The method according to [1] or [2], wherein the phosphatidylcholine is 1,2-dioleoyl-sn-glycero-3-phosphocholine (DOPC), palmitoyl-oeoyl phosphatidylcholine (POPC), or 1,2-dieicosenoyl-sn-glycero-3-phosphocholine (DEPC).

[4] The method according to [3], wherein the phosphatidylcholine is DOPC.

[5] The method according to [1], wherein step (a) comprises dissolving and mixing DOPE, DOPC, and DC-6-14 in alcohol.

[6] The method according to any of [1] to [5], which further comprises step (d) of mixing the lyophilized product obtained in step (c) in a buffer.

[7] A pharmaceutical composition used for topical administration aimed at treatment of peritoneal metastasis of gastric cancer, ovarian cancer, and pancreatic cancer, which comprises a lipid mixture comprising dioleylphosphatidylethanolamine (DOPE), phosphatidylcholine, and a cationic lipid, wherein the phosphatidylcholine has one or more features selected from (i) to (iii) below:

(i) the phosphatidylcholine comprises at least one unsaturated fatty acid chain containing a carbon-to-carbon double bond;

(ii) the phosphatidylcholine comprises at least one unsaturated fatty acid chain containing a cis-form carbon-to-carbon double bond; and (iii) the phosphatidylcholine has a phase transition temperature below 0° C., and short hairpin RNA (shRNA) capable of inhibiting thymidylate synthase expression via RNAi (TS-shRNA).

[8] The pharmaceutical composition according to [7], wherein the cationic lipid is O,O'-ditetradecanoyl-N-(α-trimethylammonioacetyl)diethanolamine chloride (DC-6-14).

[9] The pharmaceutical composition according to [7], wherein the phosphatidylcholine is DOPC.

[10] The pharmaceutical composition according to [7], wherein the lipid mixture consists of DOPE, DOPC, and DC-6-14.

[11] The pharmaceutical composition according to [10], which comprises DOPE, DOPC, and DC-6-14 at a molar ratio of 3:2:5.

[12] The pharmaceutical composition according to any of [7] to [11], wherein the shRNA consists of the nucleotide sequence as shown in SEQ ID NO: 8.

[13] The pharmaceutical composition according to any of [7] to [12], which is used in combination with a cancer chemotherapeutic agent.

[14] A combined product comprising the pharmaceutical composition according to any of [7] to [13] and a cancer chemotherapeutic agent.

[15] The combined product according to [14], wherein the cancer chemotherapeutic agent is selected from the group consisting of an antitumor agent having microtubule depolymerization inhibitory action, a deoxycytidine derivative, and an antitumor agent having TS inhibitory action.

This description includes part or all of the content as disclosed in Japanese Patent Application No. 2014-221062, which is a priority document of the present application.

Effects of the Invention

The present invention can provide an industrial method for lipoplex production that enables easy, simultaneous production of lipoplex-generating powders which produce lipoplex by merely suspending it in a solvent such as water. This would obviate the need for a complicated process of lipoplex production comprising generating a lipid mixture with the use of a large quantity of an organic solvent, such as chloroform or cyclohexane, being subjected to lyophilization, dispersing the resulting lipid mixture in a solvent, such as water, and then mixing the resulting dispersion with an aqueous solution of RNAi molecules.

According to the present invention, also, the need for a complicated process of lipoplex preparation that requires extensive labor at a prescription department of a hospital can be eliminated.

With the use of the lipoplex of the present invention, RNAi molecules capable of inhibiting tumor growth can also be efficiently delivered to tumor cells.

BRIEF DESCRIPTION OF THE DRAWINGS

FIG. 1 shows the results of comparison of physical properties (i.e., particle diameter, polydispersity index, and zeta potential) of a conventional preparation, novel preparation (1), and novel preparation (2): the conventional preparation prepared by dissolving a lipid mixture consisting of DOPC, DOPE, and DC-6-14 obtained by a known technique in an organic solvent (cyclohexane/ethanol (95/5 (v/v))), lyophilizing the resulting solution, dispersing the resulting lyophilized product in water to prepare a solution, and mixing an aqueous solution of RNAi molecules therewith; and novel preparation (1) and novel preparation (2) obtained by the method according to the present invention: novel preparation (1) prepared by dissolving a lipid mixture consisting of DOPC, DOPE, and DC-6-14 in an organic solvent (cyclohexane/ethanol (95/5 (v/v))), lyophilizing the resulting solution, and homogeneously dissolving the resulting lyophilized product in ethanol to prepare a solution, adding the resulting solution dropwise to a homogeneous solution of RNAi molecules with agitation, lyophilizing the resulting solution, and dispersing the resulting lyophilized product in water; and novel preparation (2) prepared by homogeneously dissolving lipids (i.e., DOPC, DOPE, and DC-6-14) in ethanol to prepare a homogenous solution, dissolving the resulting homogenous solution dropwise in a homogeneous aqueous solution of RNAi molecules with agitation to prepare a water/ethanol solution, lyophilizing the resulting water/ethanol solution, and dispersing the resulting lyophilized product in water.

FIG. 2 shows photographs demonstrating the results of comparison of the TS-shRNA-retaining capacity of a conventional preparation obtained by a known technique, novel preparation (1) obtained by the method of the present invention, and novel preparation (2) obtained by the method of the present invention.

FIG. 3 shows a chart demonstrating the results of comparison and analysis of the inhibitory effects on the tumor target gene (TS mRNA) via real-time RT-PCR achieved by intraperitoneal administration of the conventional preparation obtained by a known technique, novel preparation (1) obtained by the method of the present invention, and novel preparation (2) obtained by the method of the present invention to mouse models of gastric cancer peritoneal metastasis (*: $P<0.05$; **: $P<0.01$).

FIG. 5-1 shows photographs demonstrating the results of analysis using IVIS of tumor growth inhibitory effects of administration of the TS-shRNA-carrying lipoplex (i.e., novel preparation (2)) alone, Paclitaxel alone, and the TS-shRNA-carrying lipoplex (i.e., novel preparation (2)) in combination with Paclitaxel on mouse models of ovarian cancer peritoneal metastasis.

FIG. 5-2 shows a chart demonstrating the results of quantification of the tumor growth in the abdominal cavity based on the image data shown in FIG. 5-1.

FIG. 5-3 shows the results demonstrated in FIG. 5-2 in the form of a logarithmic chart.

FIG. 5-4 shows a chart demonstrating the life-prolonging effects observed in the control group, the group subjected to administration of the TS-shRNA-carrying lipoplex (i.e., novel preparation (2)) alone, the group subjected to administration of Paclitaxel alone, and the group subjected to administration of Paclitaxel in combination with the TSshRNA-carrying lipoplex (i.e., novel preparation (2)) in animal experiments shown in FIG. 5-1.

FIG. 5-5 shows a chart demonstrating a change in TS-shRNA concentration in the ascites and in the blood assayed via RT-PCR after intraperitoneal administration of the TS-shRNA-carrying lipoplex (i.e., novel preparation (2)) to a mouse model of ovarian cancer peritoneal metastasis.

FIG. 6-1 shows a chart demonstrating the results of quantification using IVIS of the tumor growth analyzed based on the image data from mouse models of pancreatic cancer peritoneal metastasis subjected to administration of the TS-shRNA-carrying lipoplex (i.e., novel preparation (2)) alone, Paclitaxel alone, and the TS-shRNA-carrying lipoplex (i.e., novel preparation (2)) in combination with Paclitaxel.

FIG. 6-2 shows the results demonstrated in FIG. 6-1 in the form of a logarithmic chart.

FIG. 6-3 shows a chart demonstrating the life-prolonging effects observed in mouse models of pancreatic cancer peritoneal metastasis resulting from administration of the TS-shRNA-carrying lipoplex (i.e., novel preparation (2)) alone, administration of Paclitaxel alone, and administration of the TS-shRNA-carrying lipoplex (i.e., novel preparation (2)) in combination with Paclitaxel.

EMBODIMENTS FOR CARRYING OUT THE INVENTION

Figure 4:
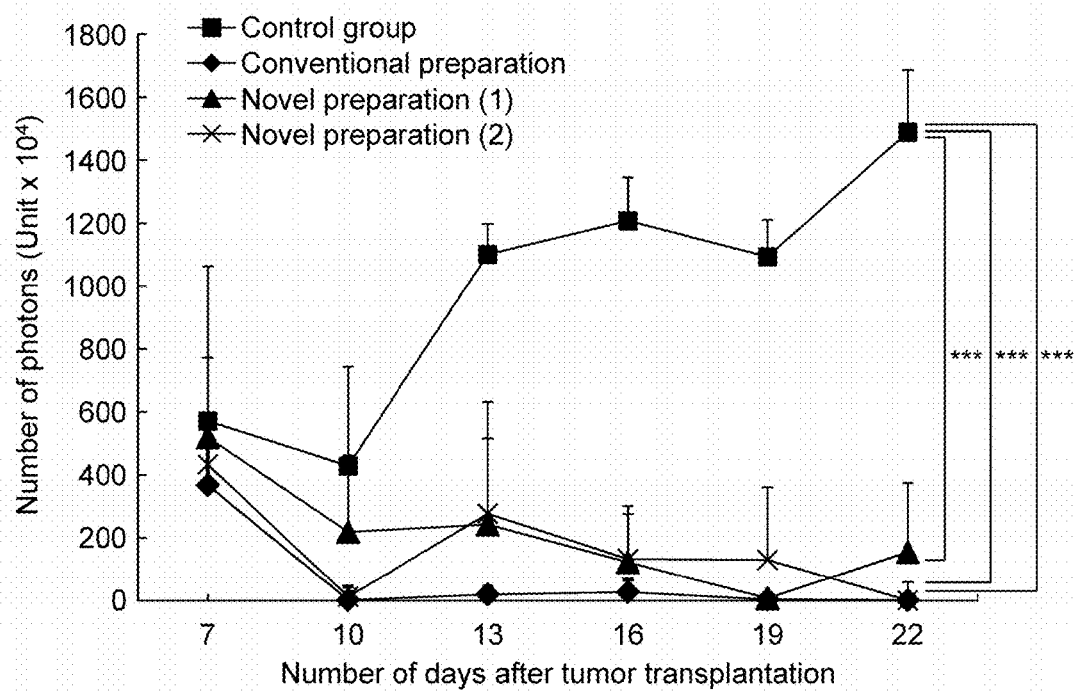
FIG. 4 shows a chart demonstrating the results of quantification of luciferase activity of groups of mouse models of gastric cancer peritoneal metastasis subjected to intraperitoneal administration of the conventional preparation, novel preparation (1), and novel preparation (2), respectively, as well as the control group (i.e., tumor growth inhibitory effects) (***: $P<0.005$).

The lipoplex of the present invention comprises a lipid mixture consisting of dioleylphosphatidylethanolamine (DOPE), phosphatidylcholine, and a cationic lipid and an RNAi molecule, or it is a complex consisting of them.

The "phosphatidylcholine" that can be used in the present invention has one or more features selected from (i) to (iii) below:

(i) the phosphatidylcholine comprises at least one unsaturated fatty acid chain containing a carbon-to-carbon double bond;

(ii) the phosphatidylcholine comprises at least one unsaturated fatty acid chain containing a cis-form carbon-to-carbon double bond; and (iii) the phosphatidylcholine has a low phase transition temperature (e.g., below 0° C., below −10° C., or below −20° C.).

Examples of such "phosphatidylcholine" include 1,2-dioleoyl-sn-glycero-3-phosphocholine (DOPC), palmitoyl-oeoyl phosphatidylcholine (POPC), and 1,2-dieicosenoyl-sn-glycero-3-phosphocholine (DEPC), with DOPC being preferable.

The "cationic lipid" that can be used in the present invention can be any substance selected from among O,O'-ditetradecanoyl-N-(α-trimethylammonioacetyl)diethanolamine chloride (DC-6-14), N,N-dioleoyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleoyloxy)propyl)-N,N,N-trimethylammonium chloride (DOTMA), N,N-dimethyl-(2,3-dioleoyloxy)propylamine (DODMA), and a derivative of any thereof. A cationic lipid is preferably DC-6-14.

The lipoplex of the present invention preferably comprises a lipid mixture consisting of DOPE, DOPC, and DC-6-14.

The proportion of DOPE, phosphatidylcholine (DOPC), and a cationic lipid (DC-6-14) in the lipoplex can be determined within a molar ratio range of 2 to 4:1 to 3:4 to 6. The proportion of DOPE:DOPC:DC-6-14 is preferably 3:2:5.

A particle size of the lipoplex of the present invention is 200 nm to 2000 nm, and preferably about 400 nm to 700 nm. The zeta potential of the lipoplex of the present invention is 30 to 60 mV, and preferably about 30 to 40 mV.

The lipoplex of the present invention can be prepared by the method comprising the following steps.

Specifically, a lyophilized product of a mixture of phosphatidylethanolamine, phosphatidylcholine, and a cationic lipid or each ingredient thereof is dissolved in alcohol.

Examples of alcohols that can be used include ethanol and methanol, with ethanol having high biotolerance being particularly preferable. Phosphatidylethanolamine, phosphatidylcholine, and a cationic lipid can be used in any form. For example, such substance can be used in powder form.

Phosphatidylethanolamine, phosphatidylcholine, and a cationic lipid may be separately dissolved in alcohol in advance, and such substances are separately fractionated and mixed to adjust the amount of the resulting mixture to the given level. Alternatively, a lyophilized product of a lipid mixture consisting of phosphatidylethanolamine, phosphatidylcholine, and a cationic lipid in the given amount described above may be dissolved in alcohol.

The amounts of phosphatidylethanolamine, phosphatidylcholine, and a cationic lipid in an alcohol mixture can be each 1 to 100 mM, and preferably 10 to 80 mM.

Phosphatidylethanolamine, phosphatidylcholine, and a cationic lipid can be dissolved in alcohol with heating. For example, heating can be carried out at 35° C. to 60° C., and preferably 40° C. to 50° C.

Subsequently, the resulting alcohol solution is added dropwise to a solution of RNAi molecules (e.g., an aqueous solution of RNAi molecules in water) with agitation, and the resulting solution is then lyophilized to obtain a lyophilized product of the lipoplex. It is preferable that an alcohol solution be mixed with a solution of RNAi molecules at 1 to 3:7 to 9.

The lyophilized product may be further mixed with an aqueous solution such as a buffer, so as to obtain a lipoplex suspension, and the resulting suspension can be administered to an organism. A buffer may be in the form of an aqueous solution that can be administered to an organism. For example, physiological saline or a carbohydrate fluid can be used. Mixing is preferably carried out for 1 to 15 minutes, and more preferably approximately 5 minutes, via agitation with the use of a vortex mixer or other means. By performing agitation in such a manner, a particle size of the lipoplex can be adjusted to the level of interest described above.

In the method for producing a lipoplex according to the present invention, the use of chloroform or cyclohexane with high toxicity and explosiveness is not necessary. Accordingly, it is not necessary to provide a highly secure explosion-proof facility in the manufacturing plant. Since ethanol with high biotolerance is selectively used, also, administration thereof to a patient would not pose any problem even in the presence of a very minor amount of a remaining solvent.

According to the present invention, in addition, a lipoplex can be easily prepared in a medical field, such as a prescription department of a hospital. Specifically, an injection vial or the like filled with the lyophilized product of the lipoplex may be provided to a medical field, such as a prescription department of a hospital, so that a solution of the lipoplex to be administered (i.e., a water dispersion) can be prepared at the time of use by merely adding a buffer thereto at a prescription department of a hospital before administration to a patient.

The lipoplex of the present invention can be used for topical administration to a patient. In the present invention, "topical administration" is not intended to systemic administration via intravenous injection or other means. Examples of topical administration include, but are not limited to, intraperitoneal, intrathoracic, intramuscular, hypodermic, endodermic, intraocular, intracerebral, intrathecal, intravaginal, intrarectal, intraorgan, and application to the epidermis. The term "topical administration" preferably refers to intracavitary administration, and more preferably intrathoracic or intraperitoneal administration.

The lipoplex of the present invention comprises, as an active ingredient, an RNAi molecule, such as siRNA or shRNA, capable of inhibiting the expression of genes encoding factors expressed in tumor cells and involved with tumor cell growth via RNAi. Examples of "genes encoding factors expressed in tumor cells and involved with tumor cell growth" include, but are not limited to, genes encoding growth regulatory factors, such as thymidylate synthase, VEGF, EGFR, PDGF, HGF, Wint, Bcl-2, and survivin, and enzymes involved in nucleic acid synthesis, such as ribonucleotide reductase and DNA polymerase. Gene information on these genes is disclosed in known databases of GenBank and the like, and siRNA or shRNA can be designed and synthesized on the basis of such gene information. shRNA that is described in detail below can be used as shRNA that can inhibit expression of thymidylate synthase via RNAi. Alternatively, a cancer chemotherapeutic agent can be used as an active ingredient.

In the lipoplex of the present invention, an RNAi molecule may be contained in a hollow portion enclosed by a lipid bilayer of a lipid mixture, or it may be bound to the outer membrane surface of a lipid bilayer. An RNAi molecule is preferably bound to the outer membrane surface of a lipid bilayer. An RNAi molecule can be bound to the outer membrane surface of a lipid bilayer by the method described above.

The lipoplex of the present invention can be used as an antitumor agent.

The lipoplex according to an embodiment of the present invention comprises shRNA that can inhibit expression of thymidylate synthase (hereafter referred to as "TS") via RNAi.

shRNA that can inhibit TS expression according to the present invention exerts TS-specific RNAi activity by targeting mRNA of TS, and it can thus inhibit TS expression remarkably. The term "targeting mRNA" used herein refers to the situation in which an antisense strand of shRNA described in detail below can hybridize under stringent conditions to the target mRNA.

Stringent conditions can be determined on the basis of the melting temperature (Tm) for nucleic acid at which a hybrid is formed in accordance with a conventional technique. Under stringent conditions, for example, washing conditions that allows maintenance of hybridization comprise generally "1×SSC, 0.1% SDS, 37° C.," more strictly "0.5×SSC, 0.1% SDS, 42° C.," and further strictly "0.1×SSC, 0.1% SDS, 65° C."

According to the present invention, shRNA comprises a sense strand comprising a nucleotide sequence identical to the nucleotide sequence of ORF encoding TS or a part thereof and an antisense strand hybridizing under stringent conditions to the sense strand. The term "nucleotide sequence identical to the nucleotide sequence of ORF or a part thereof" refers to a nucleotide sequence that is identical to a nucleotide sequence obtained by substituting thymine with uracil in the nucleotide sequence of ORF or a part thereof.

The sense strand consists of 15 to 25 nucleotides, and preferably 19 nucleotides. While the nucleotide sequence of the sense strand is preferably the same as the nucleotide sequence of ORF encoding TS, it may be substantially the same sequence; that is, a homologous sequence. Specifically, the nucleotide sequence of the sense strand may be different from the nucleotide sequence of ORF by substitution, deletion, insertion, and/or addition of one or more; that is, 1 to 3 nucleotides, preferably 1 or 2 nucleotides, and more preferably 1 nucleotide.

The antisense strand comprises a nucleotide sequence that can hybridize under stringent conditions to the sense strand. As long as it can hybridize under stringent conditions, the antisense strand may comprise a mismatch, including substitution, deletion, insertion, and/or addition of 1 to 3 nucleotides, preferably 1 or 2 nucleotides, and more preferably 1 nucleotide. The antisense strand preferably consists of a nucleotide sequence completely complementary to the sense strand.

Nucleotide sequences of the sense strand and the antisense strand can be selected on the basis of the known TS-encoding nucleotide sequence (GenBank: CR601528.1). Various methods for selecting such nucleotide sequences are known. For example, the siRNA Design Support System (Takara Bio Inc.) can be employed.

In the present invention, examples of sense strands include those consisting of the nucleotide sequences indicated below, although sense strands are not limited thereto:
5'-GUAACACCAUCGAUCAUGA-3' (SEQ ID NO: 1);
5'-GAAUACAGAGAUAUGGAAU-3' (SEQ ID NO: 3);
and 5'-CGAUCAUGAUGUAGAGUGU-3' (SEQ ID NO: 5).

```
In the present invention, shRNA preferably
comprises: the sense strand
                                          (SEQ ID NO: 1)
5'-GUAACACCAUCGAUCAUGA-3' and the antisense strand
                                          (SEQ ID NO: 2)
5'-UCAUGAUCGAUGGUGUUAC-3';

the sense strand
                                          (SEQ ID NO: 3)
5'-GAAUACAGAGAUAUGGAAU-3' and the antisense strand
                                          (SEQ ID NO: 4)
5'- AUUCCAUAUCUCUGUAUUC-3';

or the sense strand
                                          (SEQ ID NO: 5)
5'-CGAUCAUGAUGUAGAGUGU-3' and the antisense strand
                                          (SEQ ID NO: 6)
5'-ACACUCUACAUCAUGAUCG-3'.
```

In the present invention, shRNA more preferably comprises the sense strand consisting of the nucleotide sequence as shown in SEQ ID NO: 1 and the antisense strand consisting of the nucleotide sequence as shown in SEQ ID NO: 2.

A sense strand and an antisense strand are connected to each other through a linker, they are folded when the linker forms a loop, and the antisense strand and the sense strand hybridize to each other to form a double-stranded portion.

As long as a linker included in the shRNA molecule can connect the sense strand to the antisense strand and form a stem-loop structure, it may be a polynucleotide or non-polynucleotide linker. A linker is preferably, but is not particularly limited to, a polynucleotide linker consisting of 2 to 22 nucleotides known in the art. Specific examples thereof include UAGUGCUCCUGGUUG (SEQ ID NO: 7), UUCAAGAGA, CCACC, CUCGAG, CCACACC, UUCAAGAGA, AUG, CCC, and UUCG, with UAGUG-CUCCUGGUUG (SEQ ID NO: 7) being preferable.

In the present invention, shRNA comprises an overhang consisting of two or more nucleotides at the 3' end.

In the present invention, the term "overhang" refers to a nucleotide added to the 3' end of the antisense strand that does not have a nucleotide capable of complementarily binding to a corresponding position of the sense strand. If an antisense strand does not have an overhang at the 3' end, the degree of TS expression inhibition caused by shRNA decreases by about 40% to 60%, compared with a case in which an antisense strand has an overhang. Types and numbers of nucleotides constituting the overhang are not particularly limited. For example, sequences consisting of 1 to 5, preferably 1 to 3, and more preferably 1 or 2 nucleotides can be used. Specific examples include TTT, UU, and TT, with UU being preferable.

In the present invention, preferable shRNA is single-stranded RNA consisting of the nucleotide sequence as shown in SEQ ID NO: 8.

The sense or antisense strand may have the phosphorylated 5' end, and it may comprise triphosphate (ppp) bound to the 5' end, according to need.

The lipoplex having shRNA of the present invention may comprise siRNA or shRNA that can inhibit the expression of "genes encoding factors expressed in tumor cells and involved with tumor cell growth" via RNAi, in addition to shRNA that can inhibit TS expression. siRNA or shRNA as defined above can be used. shRNA that can inhibit TS expression and another siRNA or shRNA may be present on the same lipoplex or separate lipoplexes.

As described in detail in the examples below, the lipoplex having shRNA is capable of inhibiting tumor cell growth through topical administration thereof, and it can accordingly be used for treatment of cancer.

Cancers that can be treated with the use of the antitumor agent of the present invention are those exhibiting high TS expression levels. Examples thereof include, but are not particularly limited to, colorectal cancer, liver cancer, renal cancer, head and neck cancer, esophageal cancer, gastric cancer, biliary tract cancer, gallbladder and bile duct cancer, pancreatic cancer, lung cancer, breast cancer, ovarian cancer, uterine cervix cancer, uterine body cancer, bladder cancer, prostate cancer, malignant pleural mesothelioma, testicular tumor, ovarian cancer, osteosarcoma or soft-tissue osteosarcoma, skin cancer, and brain tumor. Carcinomatous pleurisy and carcinomatous peritonitis can be treated with the use of the antitumor agent of the present invention. Candidates for treatment are, for example, preferably gastric cancer, lung cancer, biliary tract cancer, liver cancer, malignant pleural mesothelioma, ovarian cancer, carcinomatous peritonitis, and carcinomatous peritonitis, and particularly preferably peritoneal metastasis of gastric cancer, ovarian cancer, and pancreatic cancer, malignant pleural mesothelioma, and lung cancer and carcinomatous pneumonia with primary lesions in the thoracic cavity.

The antitumor agent of the present invention may further comprise, in addition to a lipoplex, an excipient, a binder, a disintegrant, a lubricant, a diluent, a solubilizer, a suspending agent, an isotonizing agent, a pH regulator, a buffer, a stabilizer, a colorant, a flavoring agent, an odor improving agent, histidine, or other substances that are generally used in the production of pharmaceutical products.

Examples of excipients include lactose, sucrose, sodium chloride, glucose, maltose, mannitol, erythritol, xylitol, maltitol, inositol, dextran, sorbitol, albumin, urea, starch, calcium carbonate, kaolin, crystalline cellulose, silicic acid, methylcellulose, glycerine, sodium alginate, gum Arabic, and a mixture thereof. Examples of lubricants include purified talc, stearate, sodium borate, polyethylene glycol, and a mixture thereof. Examples of binders include simple syrup, glucose solution, starch solution, gelatin solution, polyvinyl alcohol, polyvinyl ether, polyvinyl pyrrolidone, carboxymethylcellulose, shellac, methylcellulose, ethylcellulose, water, ethanol, potassium phosphate, and a mixture thereof. Examples of disintegrants include dry starch, sodium alginate, agar powder, laminaran powder, sodium bicarbonate, calcium carbonate, polyoxyethylene sorbitan fatty acid esters, sodium lauryl sulfate, stearic acid monoglyceride, starch, lactose, and a mixture thereof. Examples of diluents include water, ethyl alcohol, macrogol, propylene glycol, ethoxylated isostearyl alcohol, polyoxylated isostearyl alcohol, polyoxyethylene sorbitan fatty acid esters, and a mixture thereof. Examples of stabilizers include sodium pyrosulfife, ethylenediaminetetraacetic acid, thioglycolic acid, thiolactic acid, and a mixture thereof. Examples of isotonizing agents include sodium chloride, boric acid, glucose, glycerine, and a mixture thereof. Examples of pH regulators and buffers include sodium citrate, citric acid, sodium acetate, sodium phosphate, and a mixture thereof.

The antitumor agent of the present invention can be administered by means of topical administration. Forms of topical administration are as defined above. The composition of the present invention can be prepared in any of various dosage forms suitable for topical administration, such as an injection, a suspension, an emulsion, or a spray. The antitumor agent of the present invention can be provided in lyophilized form, and an adequate buffer (e.g., physiological saline) can be added at the time of use thereof.

Effects of the antitumor agent of the present invention can be evaluated by administering the antitumor agent to cells or tissues originating from any of the cancers described above and to an individual afflicted with any of the cancers described above, comparing the size of the resulting tumor with the size of the tumor in cells or tissues and an individual to which the antitumor agent has not been administered (or prior to administration), and using the contraction or extinction of the tumor as the indicator. Alternatively, effects of the antitumor agent of the present invention can be evaluated by administering the antitumor agent to cells or tissues originating from any of the cancers described above and to an individual afflicted with any of the cancers described above, and determining the improved survival rate (i.e., life-prolonging effects) and reduction or disappearance of a pleural effusion or ascites, in comparison with an individual to which the antitumor agent has not been administered.

The antitumor agent of the present invention can be used in combination with existing cancer chemotherapy or a cancer chemotherapeutic agent. Cancer chemotherapy or a cancer chemotherapeutic agent that can be used in combination with the antitumor agent of the present invention is not particularly limited, provided that it can modify tumor conditions, so that the lipoplex of the present invention can easily invade into tumor tissue. Examples of existing cancer chemotherapeutic agents include antitumor agents having microtubule depolymerization inhibitory action, such as Taxol® (Bristol-Myers Squibb) and Taxotere® (Sanofi-Aventis), that are effective for patients with peritoneal metastasis of gastric cancer and ovarian cancer and antitumor agents comprising deoxycytidine derivatives, such as Gemcitabine® (Eli Lilly) that is effective for treatment of pancreatic cancer and pancreatic cancer peritoneal metastasis.

The antitumor agent of the present invention can be used in combination with other conventional cancer chemotherapeutic agents, in addition to or instead of the cancer chemotherapeutic agents described above. Examples of such cancer chemotherapeutic agents include cyclophosphamide, nitrogen mustard N-oxide, ifosfamide, melphalan, busulphan, mitobronitol, carboquone, thiotepa, ranimustine, nimustine, temozolomide, carmustine, pemetrexed disodium, methotrexate, 6-mercaptopurine riboside, mercaptopurine, doxifluridine, carmofur, cytarabine, cytarabine ocfosfate, enocitabine, fludarabine, pemetrexed, cisplatin, carboplatin, oxaliplatin, docetaxel, irinotecan hydrochloride, and capecitabine. One or a plurality of cancer chemotherapeutic agents selected therefrom can be used. As in the case of the cancer chemotherapeutic agent described above, shRNA can be efficiently delivered to tumor cells when the cancer chemotherapeutic agent is used in combination with the antitumor agent of the present invention. Antitumor effects achieved thereby can be remarkably higher than those achieved with the use of the cancer chemotherapeutic agent or the antitumor agent of the present invention alone.

As long as the antitumor agent of the present invention is administered in combination with the existing cancer chemotherapeutic agent, these agents can be provided in the form of a "combined product."

The antitumor agent of the present invention can be prepared in the form of a "combined product" in combination with the existing cancer chemotherapeutic agent. Such "combined product" may be a compound drug containing the antitumor agent of the present invention and the existing cancer chemotherapeutic agent as active ingredients. In addition, a single package (a formulation kit) containing the antitumor agent of the present invention and the existing cancer chemotherapeutic agent suitable for combined administration can be produced, packaged, and distributed.

The term "combined administration" can refer to not only simultaneous administration of the antitumor agent of the present invention and the existing cancer chemotherapeutic agent but also administration of the antitumor agent of the present invention and the existing cancer chemotherapeutic agent at certain intervals. The route of administration and the means for administration of the antitumor agent of the present invention may be the same or different from those of the existing cancer chemotherapeutic agent.

The dose and the administration frequency of the antitumor agent of the present invention can vary depending on factors, such as the age and the body weight of a patient and the severity of disease. The antitumor agent can be administered at a single dose appropriately selected from the range of 0.0001 mg to 100 mg in terms of the amount of shRNA per kg of the body weight 1 to 3 times every day or every 1 to 21 days.

The dose of the existing cancer chemotherapeutic agent can vary depending on factors, such as a type of a chemical substance as an active ingredient, the age and the body weight of a patient, and the severity of disease. The existing cancer chemotherapeutic agent can be administered at a single dose appropriately selected from the range of 0.0001 mg to 1000 mg per kg of the body weight 1 to 3 times every day or every 1 to 14 days. When the existing cancer chemotherapeutic agent is Paclitaxel, for example, it can be administered at a daily dose of 500 to 1000 mg intraperitoneally or intravenously every 1 to 21 days. When the existing cancer chemotherapeutic agent is a pemetrexed sodium hydrate, it can be administered at a daily dose of 500 to 1000 mg intravenously every 1 to 21 days. When the existing cancer chemotherapeutic agent is TS-1, which is a 5-FU oral antitumor agent, it can be administered 1 to 3 times a day, every day, or every 2 or 3 days. The existing cancer chemotherapeutic agent can be administered at lower doses and frequencies when used in combination with the antitumor agent of the present invention compared with a case in which it is administered alone. This can suppress or delay the development of side effects that can be caused by administration of the existing cancer chemotherapeutic agents. Examples of side effects include, but are not limited to, bone-marrow suppression, hemolytic anemia, disseminated intravascular coagulation syndrome, fulminant hepatic failure, dehydration, enteritis, interstitial pneumonia, stomatitis, gastrointestinal tract ulcer, gastrointestinal tract hemorrhage, perforation of the gastrointestinal tract, acute renal failure, muco-cutaneo-ocular syndrome, toxic epidermal necrolysis, psychoneurotic disorder, acute pancreatitis, rhabdomyolysis, and anosmia.

The present invention also relates to a method for treating cancer using the antitumor agent of the present invention. Examples of cancers that can be treated by the method include the cancers defined above. In the method of the present invention, the routes of administration and the dosages of the antitumor agent of the present invention and the existing cancer chemotherapeutic agents are as described above.

EXAMPLES

Hereafter, the present invention is described in greater detail with reference to the examples below, although the present invention is not limited to these examples.

Example 1: Preparation of Lipoplex

The reagents described below were used in Example 1.
Dioleylphosphatidylethanolamine (DOPE): Nippon Fine Chemical Co., Ltd.
1,2-Dioleoyl-sn-glycero-3-phosphocholine (DOPC): Nippon Fine Chemical Co., Ltd.
O,O'-ditetradecanoyl-N-(α-trimethylammonioacetyl)diethanolamine chloride (DC-6-14): Pharmaron
Ethanol: Wako Pure Chemical Industries, Ltd.
Sodium chloride: Wako Pure Chemical Industries, Ltd.
(TS-Targeting shRNA)

TS-targeting shRNA (hereafter referred to as "TS-shRNA") having the sequence given below was synthesized based on a known shRNA capable of inhibiting TS expression that has been confirmed to have antitumor effects (see WO 2012/161196).

TS-shRNA:
(SEQ ID NO: 8)
5'-GUAACACCAUCGAUCAUGAUAGUGCUCCUGGUUGUCAUGAUCGAUG
GUGUUACUU-3'

(1) Preparation of Lipoplex (Novel Preparation) by the Method of the Present Invention (1-1) Preparation of Lipoplex (i.e., Novel Preparation (1)) from a Lyophilized Product of a Lipid Mixture Presome DF1 (a lipid mixture comprising DOPE, DOPC, and DC-6-14 at a molar ratio of 3:2:5, manufactured by Nippon Fine Chemical Co., 100 mg) was weighed and dissolved in 1.842 ml of ethanol at room temperature to obtain a solution of a lipid mixture in ethanol.

To 66.2 μl of RNase free water, 3.8 μl of 300 μM TS-shRNA was added to obtain an aqueous TS-shRNA solution.

Subsequently, 30 μl of the solution of a lipid mixture in ethanol was gradually added dropwise to 70 μl of the aqueous TS-shRNA solution with slow agitation, so as to obtain a solution of lipoplex in ethanol/water.

The resulting solution of lipoplex in ethanol/water was frozen at −40° C. or lower and then lyophilized using a vacuum freeze dryer (LABCONCO FZ-4.5, Asahi Life Science Co., Ltd.).

To the resulting lyophilized product, 100 μl of physiological saline prepared with RNase free water (an aqueous solution of 0.9 v/w % sodium chloride) was added, and the mixture was agitated using a PresentMixer2013 for 10 seconds to obtain a lipoplex (the amount of TS-shRNA: 20 μg/100 μl).

Hereafter, the lipoplex thus obtained is indicated as "novel preparation (1)."

(1-2) Preparation of Lipoplex (Novel Preparation (2)) from Lipid Powders of DOPE, DOPC, and DC-6-14

Powders of DOPE (55.8 mg), DOPC (78.6 mg), and DC-6-14 (66.0 mg) were weighed, 1 ml each ethanol was added thereto, and the mixtures were then heated to 40° C. to obtain solutions containing 75 mM DOPE, 100 mM DOPC, and 100 mM DC-6-14, respectively.

To 4.777 μl of ethanol, 9.172 μl of the 75 mM DOPE solution, 4.586 μl of the 100 mM DOPC solution, and 11.465 μl of the 100 mM DC-6-14 solution were added to obtain a solution of the lipid mixture in ethanol containing DOPE, DOPC, and DC-6-14 at a molar ratio of 3:2:5.

Subsequently, 30 μl of the solution of a lipid mixture in ethanol was gradually added dropwise to 70 μl of the aqueous TS-shRNA solution with slow agitation to obtain a solution of lipoplex in ethanol/water.

The resulting solution of lipoplex in ethanol/water was lyophilized in the same manner as in (1-1), physiological saline prepared with RNase free water was added thereto, and the mixture was then agitated to obtain a lipoplex (the amount of TS-shRNA: 20 μg/100 μl).

Hereafter, the lipoplex thus obtained is indicated as "novel preparation (2)."

(2) Preparation of Lipoplex by a Known Technique

Powders of DOPE (0.51 mg), DOPC (0.36 mg), and DC-6-14 (0.76 mg) were weighed, and such powders were mixed and dissolved in 1.0 ml of a cyclohexane/ethanol mixture (95%/5% (V/V)). Subsequently, the resulting solution was lyophilized, cyclohexane and ethanol were removed therefrom, 50 μl of physiological saline was added, the mixture was vigorously agitated using a vortex mixer for 10 minutes to prepare a suspension, and 50 μl of an aqueous solution containing TS-shRNA (0.4 μg/μl) was introduced thereinto, so as to obtain a lipoplex (the amount of TS-shRNA: 20 μg/100 μl).

Hereafter, a lipoplex thus obtained is referred to as a "conventional preparation."

Example 2: Comparison of Equivalence of Physical Lipoplex Properties

With the use of a Zetasizer Nano ZS (Malvern), the particle diameter (d. nm), the polydispersity index (PdI), and the zeta potential (mV) of novel preparation (1) and novel preparation (2) obtained in Example 1, as well as the conventional preparation, were measured.

Figures 1, 5:
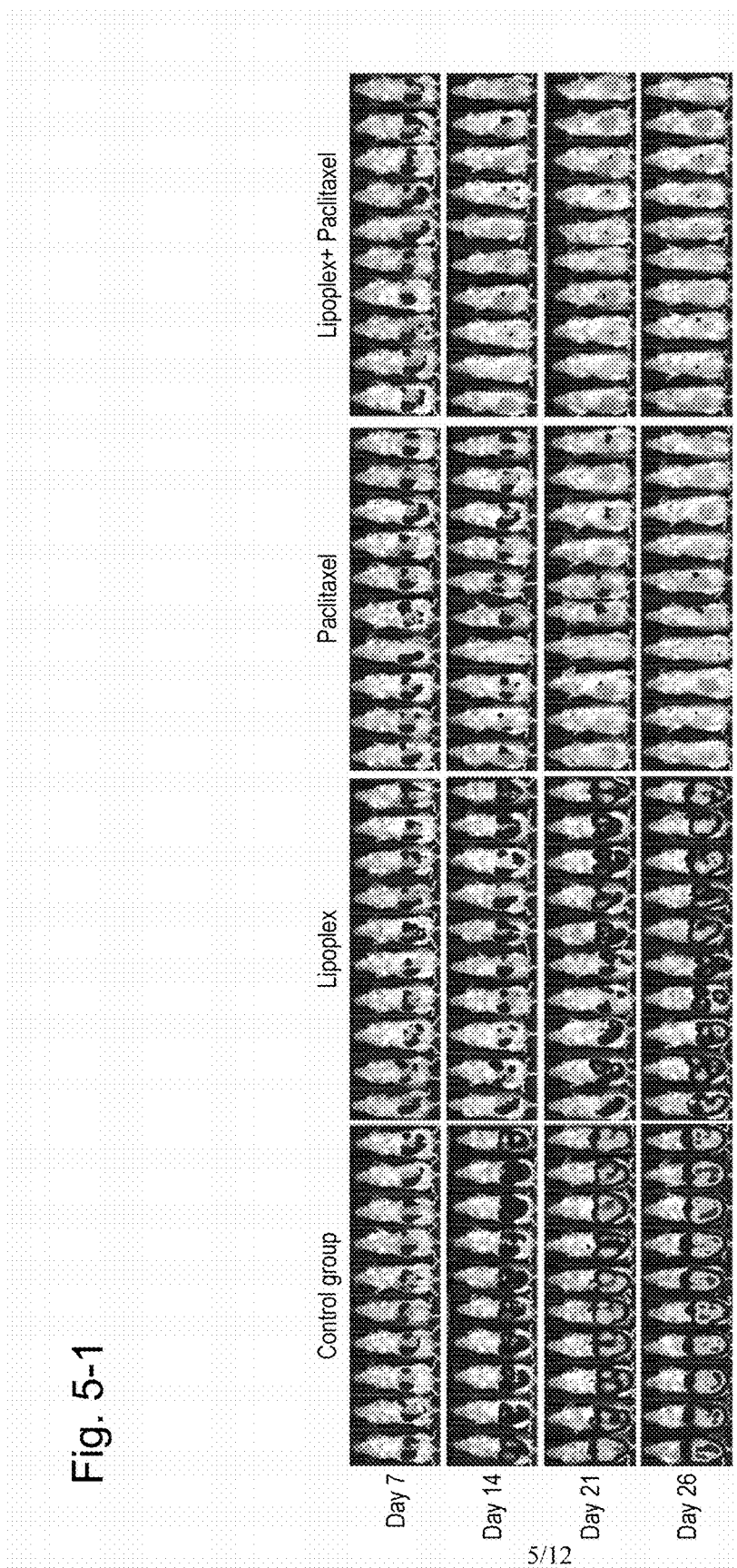

The results are shown in FIG. 1.

The results demonstrate that there are no significant differences in terms of physical properties among the conventional preparation obtained by a known technique, novel preparation (1), or novel preparation (2) obtained by the method of the present invention and that the preplex obtained by a known technique is not different from the preplex obtained by the method of the present invention in terms of physical properties.

Example 3: Evaluation of the TS-shRNA-Retaining Capacity of Lipoplex

The reagents described below were used in Example 3.
Tris: Wako Pure Chemical Industries, Ltd.
Boric acid: Wako Pure Chemical Industries, Ltd.
EDTA·2Na: Sigma-Aldrich
Agarose: Sigma-Aldrich
Ethidium bromide (EtBr): Wako Pure Chemical Industries, Ltd.

Novel preparation (1), novel preparation (2), and the conventional preparation prepared in Example 1 were evaluated in terms of shRNA-retaining capacity.

Tris (5.4 g), boric acid (2.75 g), and EDTA·2Na (0.185 g) were weighed, and distilled water was added to adjust the amount of the solution to 1 liter. Thus, TBE buffer was prepared. TBE buffer (40 ml) was added to 0.4 g of agarose, agarose was completely dissolved by boiling, 4 μl of 1 mg/ml EtBr was added thereto, the resultant was introduced onto a gel plate, and the temperature was returned to room temperature to prepare 1% agarose gel.

The gel plate was mounted on an electrophoresis apparatus (PLUS-2, CIMA Biotech), the conventional preparation, novel preparation (1), and novel preparation (2) were each diluted 10-fold and applied onto agarose gel, TBE buffer was added to an electrophoretic tank, and electrophoresis was then carried out at 100 V for 15 minutes. Thereafter, the TS-shRNA band was observed using an AE-9000N E-Graph (ATTO Corporation). Evaluation was carried out in the same manner 1 day and 3 days after the preparation of the lipoplexes.

The results are shown in FIG. 2.

Immediately after production of the conventional preparation, novel preparation (1), and novel preparation (2), no band was observed therein in the same position as that in the case of the free TS-shRNA. That is, there was substantially no free TS-shRNA in the lipoplex-containing samples. In addition, no band was observed in the same position as that in the case of TS-shRNA 3 days after the production. It was thus confirmed that the conventional preparation, novel preparation (1), and novel preparation (2) could retain TS-shRNA 3 days after the production thereof.

The results demonstrate that there is no significant difference in terms of the shRNA-retaining capacity between the lipoplex obtained by a conventional technique and the lipoplex obtained by the method of the present invention.

Example 4: Evaluation of the Inhibitory Effects of Lipoplex on the Target Gene of a Tumor Via Intraperitoneal Administration (Real-Time RT-PCR)

The reagents described below were used in Example 4.
TaqMan® Reverse Transcription Reagents: Life Technologies
FastStart Universal Probe Master (ROX): Roche
Universal ProbeLibrary #64: Roche
Universal ProbeLibrary #60: Roche
Forward primer for TS mRNA: Life Technologies

```
Nucleotide sequence:
                                    (SEQ ID NO: 9)
5'-CCC CTT CTT CTC TGG TGG A-3'

Reverse primer for TS mRNA: Life Technologies
Nucleotide sequence:
                                    (SEQ ID NO: 10)
5'-AGG AGT TGC TGT GGT TTA TCA AG-3'

Forward primer for GAPDH mRNA: Life Technologies
Nucleotide sequence:
                                    (SEQ ID NO: 11)
5'-CTC TGC TCC TCC TGT TCG AC-3'

Reverse primer for GAPDH mRNA: Life Technologies
Nucleotide sequence:
                                    (SEQ ID NO: 12)
5'-ACG ACC AAA TCC GTT GAC TC-3'
```

Novel preparation (1), novel preparation (2), and the conventional preparation prepared in Example 1 were evaluated via real-time RT-PCR in terms of inhibitory effects on the target gene of the tumor.

MKN-45 human gastric cancer cells (RIKEN, Japan) were cultured and transplanted intraperitoneally into BALB/c nu/nu mice (5-week-old, male) at $5 \times 10^6$ cells/mouse. The body weights of the mice were determined on the day of transplantation and 6 days thereafter, and mice whose body weights had decreased (i.e., mice in which the transplanted cells are considered to have engrafted) were subjected to the experiment as mouse models for peritoneal dissemination of MKN45.

The conventional preparation, novel preparation (1), or novel preparation (2) was administered intraperitoneally to different mouse models in such a manner that 20 μg of TS-shRNA would be administered to each mouse per day, and such administration was carried out three times in total (i.e., 7, 9, and 11 days after the cell transplantation). Tumors were removed from the mouse models 13 days after the cell transplantation, the tumors were homogenized with the use of a Multi-beads Shocker® (Yasui Kikai Corporation), and RNA was then extracted with the use of an RNeasy® Mini Kit (QIAGEN).

The RNA concentration in the resulting RNA extract was measured using NanoDrop 8000 (Thermo Fisher Scientific), the extract was diluted with RNase free water to adjust the RNA concentration to 1 μg/7.7 μl, and reverse transcription was then carried out with the use of TaqMan® Reverse Transcription Reagents (at 16° C. for 30 minutes, 42° C. for 30 minutes, and 85° C. for 5 minutes).

To 5 μl of the resulting cDNA solution, 15 μl of TS PCR mix or GAPDH PCR mix described below was added, real-time RT-PCR (with a cycle of 50° C. for 2 minutes and 95° C. for 10 minutes being repeated 40 times, 95° C. for 15 seconds, and 60° C. for 1 minute) with the use of StepOne-Plus™ (Life Technologies). The TS mRNA level and the GAPDH mRNA level were then measured.

| TS PCR mix (10 samples) | |
|---|---|
| ROX | 100 μl |
| Universal probe #64 | 0.45 μl |
| Forward primer for TS mRNA | 1.8 μl |
| Reverse primer for TS mRNA | 1.8 μl |
| RNase free water | 45.95 μl |
| Total | 150 μl |

| GAPDH PCR mix (10 samples) | |
|---|---|
| ROX | 100 μl |
| Universal probe #60 | 0.45 μl |
| Forward primer for GAPDH mRNA | 1.8 μl |
| Reverse primer for GAPDH mRNA | 1.8 μl |
| RNase free water | 45.95 μl |
| Total | 150 μl |

Figures 3, 5:
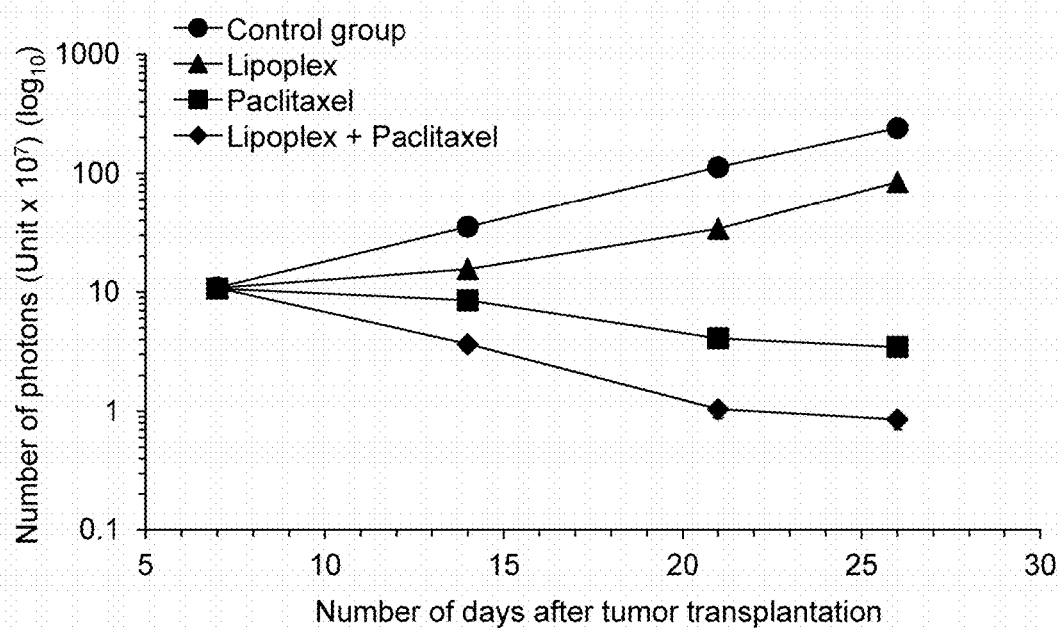

The results are shown in FIG. 3. In FIG. 3, the TS mRNA level measured via real-time RT-PCR and corrected for the GAPDH mRNA level is indicated as the "TS mRNA expression level" relative to the level (i.e., 100%) designated for the control group of mouse models to which a 9% sucrose solution had been administered without lipoplex.

In all the groups subjected to administration of the conventional preparation, novel preparation (1), and novel preparation (2), TS mRNA expression levels significantly decreased by approximately 30%, in comparison with the control group. Thus, the lipoplex obtained by a conventional technique and the lipoplex obtained by the method of the present invention were found to be capable of suppressing the expression of the target gene of the tumor that had spread to the peritoneum to a significant extent. It was also found that there had been no significant difference in such effects between the lipoplex obtained by a conventional technique and the lipoplex obtained by the method of the present invention.

Example 5: Evaluation of the Inhibitory Effects of Lipoplex on the Target Gene of Tumor Via Intraperitoneal Administration (In Vivo Imaging Systems: IVIS)

The reagents described below were used in Example 5.
Luciferin: Wako Pure Chemical Industries, Ltd.
PBS: Nissui Pharmaceutical Co., Ltd.
(Luciferase (Luc)-Targeting shRNA)

Luc-targeting shRNA (hereafter referred to as "Luc-shRNA") has the sequence shown below.

```
Luc-shRNA:
                                    (SEQ ID NO: 13)
5'-CUUACGCUGAGUACUUCGAUAGUGCUCCUGGUUGUCGAAGUACUC
AGCGUAAGUU-3'
```

In Example 5, Luc-shRNA-carrying lipoplexes were prepared with the use of luciferase-targeting shRNA (Luc-shRNA) in the same manner as in Example 1, except that Luc-shRNA was used instead of shRNA, and the inhibitory effects of novel preparation (1), novel preparation (2), and the conventional preparation on the target gene of the tumor were evaluated using IVIS.

NCI-N87 luciferase-expressing human gastric cancer cells (NCI-N87-Luc, Summit Pharmaceuticals International Corporation) were cultured and transplanted intraperitoneally into BALB/c nu/nu mice (5-week-old, male, Japan SLC, Inc.) at 4×10$^6$ cells/mouse to prepare mouse models for peritoneal dissemination of NCI-N87-Luc.

The conventional preparation, novel preparation (1), or novel preparation (2) was administered intraperitoneally to different mouse models in such a manner that 20 μg of Luc-shRNA would be administered to each mouse per day, and such administration was carried out five times in total (i.e., 8, 11, 14, 17, and 20 days after the cell transplantation). Luciferin was dissolved with PBS to a concentration of 7.5 mg/ml, 10 μl of luciferin was administered intraperitoneally 7, 10, 13, 16, 19, and 22 days after the cell transplantation, and the luciferase activity of the tumor was observed using IVIS (Xenogen, Alameda, Calif., U.S.A.). Mouse models to which no lipoplexes had been administered but to which a 9% sucrose solution had been added were employed for the control group.

With the use of image data demonstrating the results, a chart demonstrating the results of quantification of luciferase activity in the abdominal cavity is provided (FIG. 4).

In the control group, an increase was observed in luciferase activity with the elapse of time. This indicates the tumor growth in the abdominal cavity. In the groups subjected to intraperitoneal administration of the conventional preparation, novel preparation (1), and novel preparation (2) carrying Luc-shRNA, a significant decrease was observed in luciferase activity after the first administration. During the experiment (up to 22 days after the cell transplantation), luciferase activity did not increase again (FIG. 4).

While luciferase-targeting Luc-shRNA was used in Example 5, it would be unlikely that such Luc-shRNA would affect the tumor growth. In fact, the tumor weights of the groups of mice were measured 24 days after the cell transplantation, and no significant differences were observed among the groups. Thus, administration of Luc-shRNA-carrying lipoplex was found to selectively inhibit the luciferase activity of the tumor. The results demonstrate that TS-shRNA activity of the lipoplex obtained by a conventional technique is the same as that of the novel lipoplex according to the method of the present invention.

Example 6: Evaluation of the Therapeutic Effects of Lipoplex (Novel Preparation (2)) on Peritoneal Dissemination of Ovarian Cancer Via Intraperitoneal Administration Therapeutic effects of the TS-shRNA-carrying lipoplex (i.e., novel preparation (2)) prepared in the same manner as in Example 1 on peritoneal dissemination of ovarian cancer were evaluated.

OVCAR-3 luciferase-expressing human ovarian cancer cells (OVCAR-3-luc, Pharmaron) were cultured and transplanted intraperitoneally into BALB/c nu/nu mice (6- to 8-week-old, female, Beijing HFK Bio-Technology Co., Ltd.) at 1.5×10$^7$ cells/mouse to prepare mouse models for peritoneal dissemination of OVCAR-3-luc.

In Example 6, the lipoplex (novel preparation (2)), Paclitaxel (Taxol, Pharmaron), or the lipoplex (novel preparation (2)) in combination with Paclitaxel was administered to different mouse models. A 9% sucrose solution was administered to the control group.

The lipoplex (novel preparation (2)) was administered intraperitoneally to mouse models in such a manner that 20 μg of TS-shRNA would be administered to each mouse per day, and such administration was carried out four times in total (i.e., 8, 11, 14, and 17 days after the cell transplantation). Paclitaxel was administered intraperitoneally to the relevant group of mouse models four times in total (i.e., 8, 11, 14, and 17 days after the cell transplantation) at 15 mg/kg.

Luciferin was dissolved with PBS to a concentration of 7.5 mg/ml, 10 μl of luciferin was administered intraperitoneally 7, 14, 21, and 26 days after the cell transplantation, and luciferase activity of the tumor was observed using IVIS.

The results are shown in FIG. 5-1. With the use of the image data shown in FIG. 5-1, a chart demonstrating the results of quantification of luciferase activity in the abdominal cavity (FIG. 5-2) and a logarithmic chart thereof (FIG. 5-3) are provided.

In the control group, an increase was observed in luciferase activity with the elapse of time. This indicates tumor growth in the abdominal cavity. In the groups subjected to intraperitoneal administration of the TS-shRNA-carrying lipoplex, an increase in luciferase activity was suppressed, compared with the control group. This indicates that tumor growth was suppressed in the abdominal cavity. In addition, the highest tumor growth inhibitory effects were observed in the group subjected to administration of the lipoplex in combination with Paclitaxel.

FIG. 5-4 shows survival periods of the mouse models.

In comparison with the control group, significantly strong life-prolonging effects were observed in the group subjected to administration of the lipoplex in combination with Paclitaxel.

FIG. 5-5 shows the results of measurement via RT-PCR of a change in TS-shRNA concentration in the blood and the ascites of mouse models subjected to administration of the lipoplex.

The results demonstrate a long half-life of approximately 8 hours in the ascites while TS-shRNA had not leaked into the blood.

Example 7: Evaluation of the Therapeutic Effects of Lipoplex (Novel Preparation (2)) on Peritoneal Dissemination of Pancreatic Cancer Via Intraperitoneal Administration The therapeutic effects of the TS-shRNA-carrying lipoplex (i.e., novel preparation (2)) prepared in the same manner as in Example 1 on peritoneal dissemination of pancreatic cancer were evaluated.

Luciferase-expressing human pancreatic cancer cells PANC-1 (PANC-1-luc, Pharmaron) were cultured and transplanted intraperitoneally into BALB/c nu/nu mice (6- to 8-week-old, female, Beijing HFK Bio-Technology Co., Ltd.) at 1.0×10$^7$ cells/mouse to prepare mouse models for peritoneal dissemination of PANC-1-luc.

In Example 7, the lipoplex (novel preparation (2)), Paclitaxel (Taxol, Pharmaron), or the lipoplex (novel preparation (2)) in combination with Paclitaxel was administered to different mouse models. A 9% sucrose solution was administered to the control group.

The lipoplex (novel preparation (2)) was administered intraperitoneally to mouse models in such a manner that 20 μg of TS-shRNA would be administered to each mouse per day, and such administration was carried out four times in total (i.e., 8, 11, 14, and 17 days after the cell transplantation). Paclitaxel was administered intraperitoneally to the relevant group of mouse models four times in total (i.e., 8, 11, 14, and 17 days after the cell transplantation) at 10 mg/kg.

Luciferin was dissolved with PBS to a concentration of 7.5 mg/ml, 10 μl of luciferin was administered intraperitoneally 7, 14, 21, and 25 days after the cell transplantation, and the luciferase activity of the tumor was observed using IVIS.

A chart demonstrating luciferase activity in the abdominal cavity quantified on the basis of the image data obtained with the use of IVIS (FIG. 6-1) and a logarithmic chart thereof (FIG. 6-2) are provided.

In the control group, an increase was observed in luciferase activity with the elapse of time. This indicates tumor growth in the abdominal cavity. In the groups subjected to administration of the lipoplex (novel preparation (2)), Paclitaxel (Taxol, Pharmaron), or the lipoplex (novel preparation (2)) in combination with Paclitaxel, an increase in luciferase activity was suppressed, compared with the control group. This indicates that tumor growth was suppressed in the abdominal cavity. In particular, strong tumor suppression effects were observed in the group subjected to administration of Paclitaxel and in the group subjected to administration of the lipoplex in combination with Paclitaxel.

Figures 1, 6:
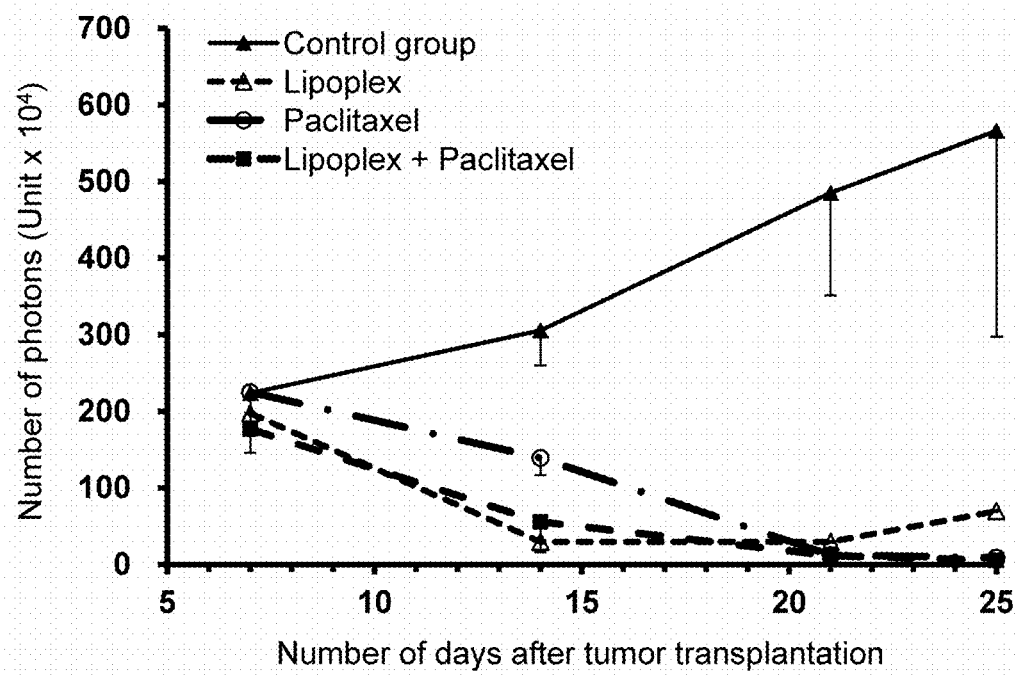
Figures 3, 6:
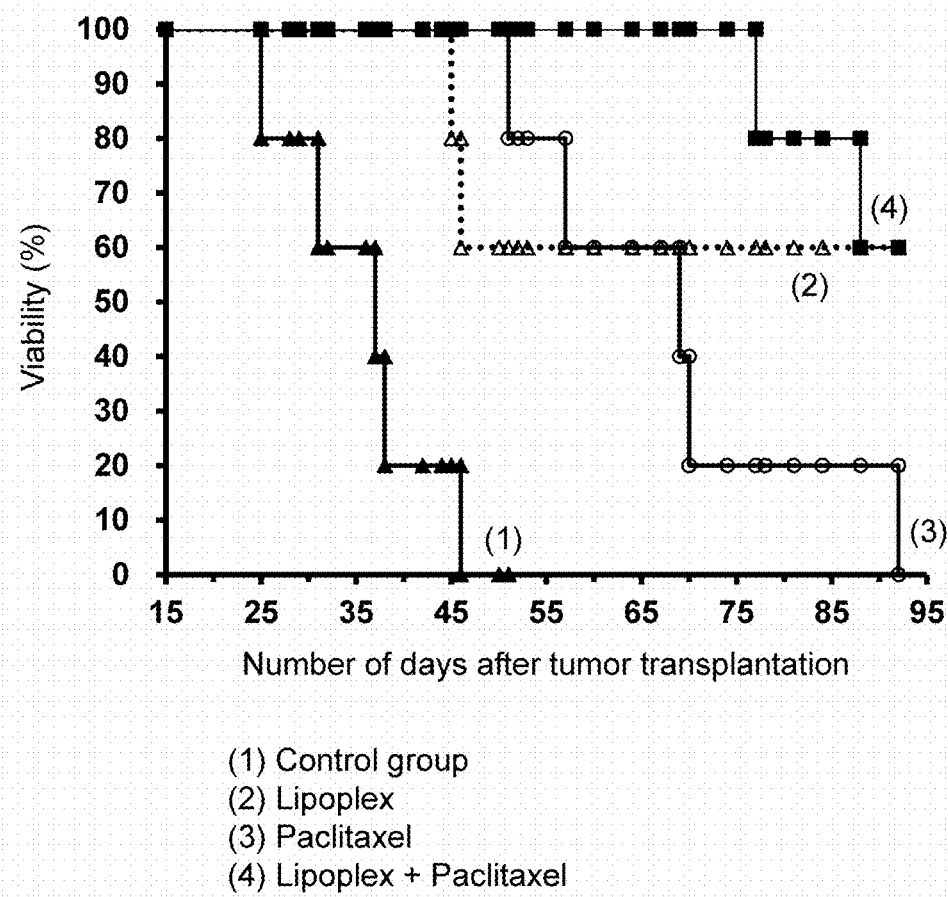

FIG. 6-3 shows survival periods of the mouse models.

In comparison with the control group, significantly strong life-prolonging effects were observed in the group subjected to administration of the lipoplex in combination with Paclitaxel.

INDUSTRIAL APPLICABILITY

According to the present invention, lipoplexes can be produced with the exclusive use of a solvent having high biotolerance without the use of an organic solvent that is highly toxic or highly explosive, such as chloroform or cyclohexane. Accordingly, the present invention is optimal for industrial production methods for pharmaceutical preparations. In medical settings, such as a prescription department of a hospital, complicated processes for drug preparation comprising separately preparing water dispersions of lipid mixtures and aqueous solutions of RNAi molecules and then mixing them together can be avoided. In addition, a fluid to be administered to a patient can be prepared by adding physiological saline or a carbohydrate fluid to lipoplex powder and mildly agitating the mixture. Accordingly, the labor and cost required for drug preparation at a prescription department of a hospital can be reduced to a significant extent.

Further, topical administration that is suitable for a given purpose of administration, such as intraperitoneal administration for patients with peritoneal metastasis of gastric cancer, ovarian cancer, or pancreatic cancer (i.e., a state near the end stage of the relevant cancer) or intrathoracic administration for patients with malignant pleural mesothelioma, lung cancer, or carcinomatous pneumonia with a primary lesion observed in the thoracic cavity, may be performed. Thus, RNAi molecules can be efficiently delivered to the target tumor cell, and tumor growth can be efficiently inhibited. The present invention is expected to make significant contributions in the field of drug delivery and cancer treatment.

All publications, patents, and patent applications cited herein are incorporated herein by reference in their entirety.

The invention claimed is:

1. A method for producing a lipoplex comprising dioleylphosphatidylethanolamine (DOPE), phosphatidylcholine, a cationic lipid, and RNAi molecules, comprising steps of:
   (a) dissolving in alcohol
      dioleylphosphatidylethanolamine (DOPE),
      phosphatidylcholine, wherein the phosphatidylcholine is 1,2-dioleoyl-sn-glycero-3-phosphocholine (DOPC), palmitoyl-oeoyl phosphatidylcholine (POPC), or 1,2-dieicosenoyl-sn-glycero-3-phosphocholine (DEPC), and
      a cationic lipid, wherein the cationic lipid is O,O'-ditetradecanoyl-N-(α-trimethylammonioacetyl)diethanolamine chloride (DC-6-14);
   (b) adding the alcohol solution obtained in (a) dropwise to a solution of RNAi molecules with agitation; and
   (c) lyophilizing the solution obtained in (b).

2. The method according to claim 1, wherein the phosphatidylcholine is DOPC.

3. The method according to claim 1, wherein step (a) comprises dissolving and mixing DOPE, DOPC, and DC-6-14 in alcohol.

4. The method according to any one of claim 1, 2, or 3, which further comprises step (d) of mixing the lyophilized product obtained in step (c) in a buffer.

* * * * *

SEQUENCE LISTING

```
<160> NUMBER OF SEQ ID NOS: 13

<210> SEQ ID NO 1
<211> LENGTH: 19
<212> TYPE: RNA
<213> ORGANISM: Artificial
<220> FEATURE:
<223> OTHER INFORMATION: synthetic oligonucleotide

<400> SEQUENCE: 1
guaacaccau cgaucauga                                                   19

<210> SEQ ID NO 2
<211> LENGTH: 19
<212> TYPE: RNA
<213> ORGANISM: Artificial
<220> FEATURE:
<223> OTHER INFORMATION: synthetic oligonucleotide

<400> SEQUENCE: 2
ucaugaucga ugguguuac                                                   19

<210> SEQ ID NO 3
<211> LENGTH: 19
<212> TYPE: RNA
<213> ORGANISM: Artificial
<220> FEATURE:
<223> OTHER INFORMATION: synthetic oligonucleotide

<400> SEQUENCE: 3
gaauacagag auauggaau                                                   19

<210> SEQ ID NO 4
<211> LENGTH: 19
```

```
<212> TYPE: RNA
<213> ORGANISM: Artificial
<220> FEATURE:
<223> OTHER INFORMATION: synthetic oligonucleotide

<400> SEQUENCE: 4
auuccauauc ucuguauuc                                                19

<210> SEQ ID NO 5
<211> LENGTH: 19
<212> TYPE: RNA
<213> ORGANISM: Artificial
<220> FEATURE:
<223> OTHER INFORMATION: synthetic oligonucleotide

<400> SEQUENCE: 5
cgaucaugau guagagugu                                                19

<210> SEQ ID NO 6
<211> LENGTH: 19
<212> TYPE: RNA
<213> ORGANISM: Artificial
<220> FEATURE:
<223> OTHER INFORMATION: synthetic oligonucleotide

<400> SEQUENCE: 6
acacucuaca ucaugaucg                                                19

<210> SEQ ID NO 7
<211> LENGTH: 15
<212> TYPE: RNA
<213> ORGANISM: Artificial
<220> FEATURE:
<223> OTHER INFORMATION: synthetic oligonucleotide

<400> SEQUENCE: 7
uagugcuccu gguug                                                    15

<210> SEQ ID NO 8
<211> LENGTH: 55
<212> TYPE: RNA
<213> ORGANISM: Artificial
<220> FEATURE:
<223> OTHER INFORMATION: synthetic oligonucleotide

<400> SEQUENCE: 8
guaacaccau cgaucaugau agugcuccug guugucauga ucgauggugu uacuu         55

<210> SEQ ID NO 9
<211> LENGTH: 19
<212> TYPE: DNA
<213> ORGANISM: Artificial
<220> FEATURE:
<223> OTHER INFORMATION: primer

<400> SEQUENCE: 9
ccccttcttc tctggtgga                                                19

<210> SEQ ID NO 10
<211> LENGTH: 23
<212> TYPE: DNA
<213> ORGANISM: Artificial
<220> FEATURE:
<223> OTHER INFORMATION: primer

<400> SEQUENCE: 10
```

```
aggagttgct gtggtttatc aag                                          23

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
ctctgctcct cctgttcgac                                              20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
acgaccaaat ccgttgactc                                              20

<210> SEQ ID NO 13
<211> LENGTH: 55
<212> TYPE: RNA
<213> ORGANISM: Artificial
<220> FEATURE:
<223> OTHER INFORMATION: synthetic oligonucleotide

<400> SEQUENCE: 13
cuuacgcuga guacuucgau agugcuccug guugucgaag uacucagcgu aaguu       55
```